United States Patent [19]

Miyake et al.

[11] Patent Number: 5,210,224
[45] Date of Patent: May 11, 1993

[54] PROCESS FOR PREPARING LANKACIDIN CARBAMATE DERIVATIVES

[75] Inventors: Akio Miyake, Hirakata; Tatsuhiko Kawai, Sanda, both of Japan

[73] Assignee: Takeda Chemical Industries, Ltd., Osaka, Japan

[21] Appl. No.: 552,687

[22] Filed: Jul. 11, 1990

[30] Foreign Application Priority Data

Jul. 25, 1989 [JP] Japan .................. 1-191818

[51] Int. Cl.$^5$ .......................... C07D 315/00
[52] U.S. Cl. .......................... 549/270
[58] Field of Search .................. 549/270

[56] References Cited

U.S. PATENT DOCUMENTS

| | | |
|---|---|---|
| 3,676,300 | 7/1972 | Yamamoto et al. |
| 3,691,181 | 9/1972 | Kishi et al. ............ 549/270 |
| 4,914,206 | 4/1990 | Minamida et al. ...... 549/270 |

OTHER PUBLICATIONS

Barcelo et al., Journal of Synthetic Organic Chemistry, Synthesis, 1986, pp. 627–632.

Primary Examiner—C. Warren Ivy
Assistant Examiner—A. A. Owens
Attorney, Agent, or Firm—Wenderoth, Lind & Ponack

[57] ABSTRACT

A process for preparing a lankacidine carbamate derivative of the formula

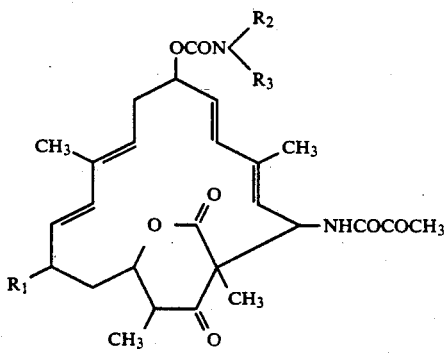

or a salt thereof, by the reaction of a lankacidine 8-substituted carbonate with an amine, wherein $R_1$ is a hydroxy group or an alkanoyloxy group; and $R_2$ and $R_3$ are each a hydrogen atom, an optionally substituted lower alkyl group, a cycloalkyl group or a phenyl group; or $R_2$ and $R_3$ together with an adjacent nitrogen atom to which they bond form an optionally substituted heterocyclic group.

3 Claims, No Drawings

PROCESS FOR PREPARING LANKACIDIN CARBAMATE DERIVATIVES

BACKGROUND OF THE INVENTION

1. Field of the Invention

The present invention relates to a process for preparing lankacidin carbamate derivatives having antimicrobial activities.

2. Prior Art

Lankacidines are antibiotics which are produced and accumulated by cultivating a Streptomyces strain and have the structure represented by the formula:

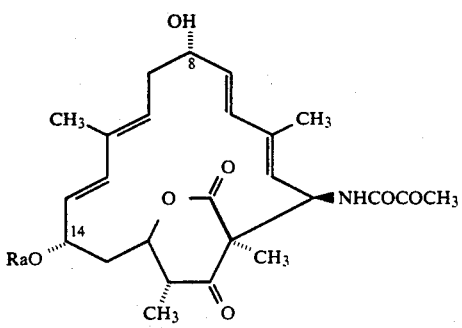

In the above formula, where Ra is $COCH_3$, the compound is lankacidin A, and where Ra is H, it is lankacidin C. Known derivatives of the lanacidins are, for example, those having an ester group at the 8 and/or 14 positions of lanacidin C [see Kagaku & Seibutsu (Chemistry and Organism, Vol. 15, pp. 337–342 (1977)): Journal of the Takeda Research Laboratories, Vol. 41, pp. 81–113 (1982)], those having an acyloxy group or the like at 8 and/or 14 positions thereof [see The Journal of Antibiotics, Vol. 26, pp 647 (1973)], and those having 8-substituted alkyl ester, 8-carbonate ester and 8-substituted carbamate (Japanese Published Unexamined Patent Application No. 240687/1987). Japanese Published Unexamined Patent Application No. 240687/1987 also discloses processes for preparing lankacidin A carbamate in which lankacidin A is reacted with isocyanates, and pentachlorophenoxy- or 2,4,5-trichlorophenoxycarbonate of lankacidin A is reacted with amines. These known processes are, however, required to use highly toxic isocyanates or expensive polyhalogenophenoxycarbonylchloride, while their yields are not satisfactory.

SUMMARY OF THE INVENTION

The present invention is to provide an industrially advantageous process for preparing 8-lankacidin carbamate derivatives having excellent antimicrobial activities.

Thus, the present invention provides a process for preparing a compound represented by the formula [III]:

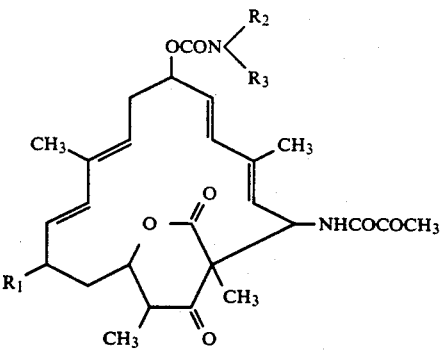

wherein $R_1$ is a hydroxy group or an alkanoyloxy group; and $R_2$ and $R_3$ are each a hydrogen atom, an optionally substituted lower alkyl group, a cycloalkyl group or a phenyl group; or $R_2$ and $R_3$ together with the adjacent nitrogen atom to which they bond form an optionally substituted heterocyclic group, or a salt thereof, comprising reacting a compound represented by the formula [I]:

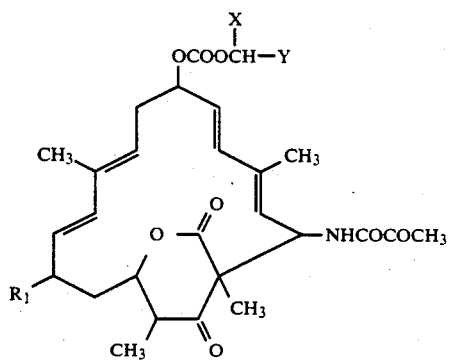

wherein $R_1$ has the same meaning as above; X is a halogen atom; and Y is a hydrogen atom, a lower alkyl group or a trihalogenoalkyl group, with a compound represented by the formula [II]:

wherein $R_2$ and $R_3$ have the same meaning as above.

DETAILED DESCRIPTION OF THE PREFERRED EMBODIMENT

The term "lower alkyl group" used in the above formula means a straight or branched chain alkyl group having 1–6 carbon atoms. Examples thereof are methyl, ethyl, n-propyl, i-propyl, n-butyl, tert-butyl, n-pentyl and n-hexyl.

The term "cycloalkyl group" used here means a cycloalkyl group having 3–6 carbon atoms. Examples thereof are cyclopropyl, cyclobutyl, cyclopentyl and cyclohexyl.

The term "alkanoyloxy group" means an alkanoyloxy having 2–6 carbon atoms. Examples thereof are acetyloxy, propionyloxy, butyryloxy, valeryloxy and hexanoyloxy. Examples of substituents for the optionally substituted lower alkyl group represented by $R_2$ or $R_3$ are a hydroxy, an amino, a mono-lower alkylamino (e.g., methylamino or ethylamino), a lower alkoxy (e.g., methoxy or ethoxy), a halogen (e.g., chlorine or bromine) and a heterocycle (e.g., pyridyl).

In the case that $R_2$ and $R_3$ together with the adjacent nitrogen atom to which they bond form a heterocyclic group, the heterocyclic group means a 4-7 membered ring having at least one nitrogen atom, and optionally an oxygen atom and/or an sulfur atom. Usually preferred is a 5 or 6 membered ring. Examples of the 5 or 6 membered rings are pyrrolidino, piperidino, morpholino and piperazino. Each of these 5 or 6 membered rings may be substituted by an optionally substituted lower alkyl (e.g., methyl, ethyl or hydroxy ethyl), a substituted phenyl (e.g., chlorophenyl) or a heterocycle (e.g., pyridyl). As Y in the formula [II], desirable is methyl, ethyl, propyl, butyl, trichloromethyl or tribromomethyl group, and particularly preferable is methyl or trichloromethyl group. As the halogen atom, desirable is chlorine, bromine or iodine.

According to the present invention, the compound of the formula [III] can be prepared by reacting a compound of the formula [I] with an amine of the formula [II]. The reaction is suitably conducted in an organic solvent optionally coexisting with water. Examples of the organic solvents are dichoromethane, chloroform, 1,2-dichloroethane, tetrahydrofuran, 1,4-dioxane, acetonitrile, ethyl acetate and methyl acetate. The amount of the amine [II] used in this reaction is suitably approximately 1-10 mol equivalents, to the compound [I]. The reaction temperature and reaction time vary within approximately 0°-100° C. and approximately 30 minutes to 24 hours, respectively, depending on the type of the amine used.

The objective compounds [III] thus obtained can be isolated and purified by a well known technique such as concentration, solvent extraction, chromatography, crystallization or recrystallization. In cases where the compound has a basic group such as an amino group or a substituted amino group as $R_2$ and $R_3$, the basic group may form an acid-addition salt. Examples of such acid-addition salts are the hydrochloride, hydrobromide, hydroiodide, nitrate, sulfate, phosphate, acetate, benzoate, maleate, fumarate, succinate, tartrate, citrate, methanesulfonate, benzenesulfonate and the like.

The resultant compounds [III] exhibit a potent antimicrobial activity on Gram-positive bacteria. As well, they exhibit an antimicrobial activity on some sorts of Gram-negative bacteria. Also, they exhibit a potent antimicrobial activity on not only macrolide-resistant *Staphyllococcus aureus* but also methicillin- and cephem-resistant *Staphyllococcus aureus* (MRSA). Further, they possess an antimicrobial activity even on mycoplasma and swine-dysentery bacillus while showing low toxicity.

As described above, the compounds [III] possess an excellent antimicrobial activity besides low toxicity. Therefore, they can be used as an antimicrobial agent for curing microbism of animals such as chickens, sheep, dogs, cats, rabbits, pigs, bovines, horses, monkeys and human beings, or for curing mycoplasma infectious diseases thereof. They can also be used as a feed additive for preventing microbism or promoting growth of the animals.

A daily dose of the compound [III] or its salt differs depending on its administration manner, the kind of animals to be administrated and the administration purpose, and is usually about 0.001-1000 mg/Kg, preferably about 0.1-300 mg/Kg.

The compound [III] or its pharmaceutically acceptable salt can be orally administered in the form of preparations such as tablets, granules, capsules and drops which can be prepared in admixture of carriers, diluents and other conventional agents in accordance with conventional techniques; and alternatively can be parenterally administered in the form of injections which can be prepared by conventional means or together with sterile carriers.

The above oral preparation, for example, tablets can be prepared by using a binder (e.g., hydroxypropylcellulose, hydroxypropylmethylcellulose, macrogol or the like), a disintegrator (e.g., starch, calcium carboxymethylcellulose or the like), a diluent (e.g., lactose, starch or the like) or a lubricant (e.g., magnesium stearate, talc or the like) can be appropriately mixed.

Further, the above parenteral preparation, for example, injection, can be prepared by appropriately mixing with an isotonization agent (e.g., glucose, D-sorbitol, D-mannitol, sodium chloride or the like), a preservative (e.g., benzyl alcohol, chlorobutanol, methyl para-hydroxybenzoate, propyl para-hydroxybenzoate or the like), a buffer (e.g., phosphate buffer solution, sodium acetate buffer solution or the like).

Hereinafter, the invention will be more fully described in conjunction with Reference Example and Examples, to which the invention is not limited.

Elution in column chromatography in the Reference Example and Examples was conducted while monitoring with TLC (Thin Layer Chromatography). In the TLC monitoring, the TLC plate used was 60F$_{254}$ manufactured by Merck Co., the developing solvent was the same one as used for eluting in the column chromatography, and the detection was conducted with a UV detector. The silica gel for the column was Kieselgel 60 (230-400 mesh) manufactured by Merck Co.

NMR spectra were measured using tetramethylsilane as an internal or external standard in a spectrometer of XL-100A (100 MHz), EM360 (60MHz), EM390 (90MHz) or T$_{60}$ (60 MHz) type, and all s values are expressed in ppm. The value shown in ( ) for a mixed solvent is a mixing ratio in volume of constituent solvents. The symbols in the Reference Example and Examples mean as follows:
s: singlet
d: doublet
t: triplet
q: quartet
ABq: AB type quartet
dd: double doublet
m: multiplet
br.: broad
J: coupling constant

REFERENCE EXAMPLE 1

Lankacidin A 8-(1-chloroethyl)carbonate

Lankacidin, A (50 g) was dissolved in 950 ml of dichloromethane, to which a solution of 19 g of 1-chloroethyl chloroformate [see Synsesis, 627 (1986)] in 40 ml of dichloromethane was added under ice cooling. To the mixture was dropwise added 10.3 g of pyridine. Then, the mixture was stirred at room temperature for an hour, mixed with 2 ml of 1- chloroethyl chloroformate and 1.5 ml of pyridine sequentially and stirred for an hour. The reaction mixture was washed with 1N—HCl, water and then dilute sodium bicarbonate solution, and dried over MgSO₄. The mixture was evaporated under reduced pressure to remove its solvent, and the resulting residue was crystallized from 500 ml of a mixture of ether-hexane (1:1) to obtain 53.7 g of the title compound.

NMR (90 MHz, CDCl$_3$)$\delta$: 1.32 (d, 3H, J=7 Hz), 1.40 (s, 3H), 1.57 (s, 3H), 1.82 (d, 3H, J=6 Hz), 1.93 (s, 3H), 2.05 (s, 3H), 2.2–2.7 (m, 5H), 2.47 (s, 3H), 4.42 (dt, 1H, J=3 & 12 Hz), 4.47 (d, 1H, J=11 Hz), 4.8–5.2 (m, 1H), 5.3–6.1 (m, 6H), 6.30 (d, 1H, J=15 Hz), 6.40 (q, 1H, J=6 Hz), 8.10 (d, 1H, J=11 Hz).

EXAMPLE 1

Lankacidin A 8-(4-methylpiperazino)carboxylate

Lankacidin 8-(1-chloroethyl)carbonate (6 g) was dissolved in 40 ml of dichloromethane, to which a solution of 6 g of N-methylpiperazine in 20 ml of dichloromethane was dropwise added under ice cooling. After stirring for 40 min., the reaction mixture was washed with 1N—HCl to remove excess amine, subsequently with a dilute sodium bicarbonate solution and water and dried over MgSO₄. The mixture was evaporated under reduced pressure to remove the solvent. The resulting residue was subjected to silica gel column chromatography (silica gel: 300 g) eluting with chloroformmethanol (30:1). The fractions including the objective compound were collected and concentrated. The resulting oily substance was then crystallized from a mixture of ether-hexane (1:1) to obtain 4.7 g of the title compound.

Melting point: 203°–207° C. (decomp.)

Elemental analysis for $C_{33}H_{45}N_3O_9 \cdot {}^{JL}H_2O$

Calcd.: C, 61.83; H, 7.33; N, 6.51.
Found: C, 61.71; H, 7.25; N, 6.79.

NMR (90 MHz, CDCl$_3$) $\delta$: 1.32 (d, 3H, J=7 Hz), 1.38 (s, 3H), 1.55 (s, 3H), 1.92 (s, 3H), 2.03 (s, 3H), 2.1–2.7 (m, 9H), 2.30 (s, 3H), 2.46 (s, 3H), 3.4–3.7 (m, 4H), 4.43 (d.d, 1H, J=3 & 12 Hz), 4.72 (d, 1H, J=11 Hz), 4.2–5.2 (m, 1H), 5.2–5.9 (m, 6H), 6.32 (d, 1H, J=15 Hz), 8.08 (d, 1H, J=11 Hz).

EXAMPLE 2

Lankacidin A 8-chloromethylcarbonate (300 mg, prepared by the process disclosed in Japanese Published Unexamined Patent Application No. 240687/1987) was dissolved in 10 ml of tetrahydrofuran, to which 100 mg of N-methylpiperazine was added at room temperature. After stirring for 3 hours, the reaction mixture was mixed with 50 ml of ethylacetate and washed with 60 ml of saturated aqueous sodium chloride solution. The resulting organic layer was dried over MgSO₄ and concentrated under reduced pressure. The residue was subjected to silica gel column chromatography (silica gel: 60 g) eluting with chloroform-methanol (30:1). The fractions including the objective compound were collected and concentrated. The residue was then crystallized from a mixture of ether-hexane (1:1) to obtain 180 mg of the compound identical to that prepared in Example 1.

EXAMPLE 3

Lankacidin A 8-iodomethylcarbonate (342 mg, prepared by the process disclosed in Japanese Published Unexamined Patent Application No. 240687/1987) was dissolved in 10 ml of tetrahydrofuran, to which 120 mg of N-methylpiperazine was added at room temperature. After stirring for 30 min. at room temperature, the reaction mixture was mixed with 50 ml of ethylacetate and washed with 60 ml of saturated aqueous sodium chloride solution. The resulting organic layer was dried over MgSO₄ and evaporated to remove the solvent. The residue was subjected to silica gel column chromatography (silica gel: 60 g) eluting with chloroform-methanol (30:1). The fractions including the objective compound were collected and concentrated. The residue was then crystallized from a mixture of ether-hexane (1:1) to obtain 193 mg of the compound identical to that prepared in Example 1.

EXAMPLES 4–13

Lankacidin A 8-(1-chloroethyl) carbonate was reacted with various amines by the method as described in Example 1 to obtain the compounds shown n Table 1.

TABLE 1

Lankacidin A 8-carbonate Derivatives

| Example No. | $-N\genfrac{}{}{0pt}{}{R^2}{R^3}$ | NMR: 11-Me, COC$\underline{H_3}$ 8-H, etc. | mp (°C.) | yield (%) |
|---|---|---|---|---|
| 4 | —NHCH₃ | 1.53(s), 2.44(s), 4.98(m), 2.77(d, J=5Hz, NHC$\underline{H_3}$) | — | 51 |
| 5 | —NH(CH₂)₂CH₃ | 1.53(s), 2.43(s), 4.98(m), 0.89(t, J=7Hz, —CH₂CH₂C$\underline{H_3}$) | — | 75 |
| 6 | —NHC₆H₅ | 1.55(s), 2.44(s), 5.05(m), 6.9~7.5(m, —C₆H₅) | 231–232 | 62 |
| 7 | —NHCH(CH₃)₂ | 1.56(s), 2.43(s), 4.95(m), 1.13(d, J=7Hz, —CH(C$\underline{H_3}$)₂) | 198–200 | 90 |
| 8 | —NHCH₂-(3-pyridyl) | 1.53(s), 2.44(s), 5.01(m), 4.47(d, J=5Hz, NHC$\underline{H_2}$—) | 192–194 | 77 |

TABLE 1-continued

Lankacidin A 8-carbonate Derivatives

| Example No. | −N<R²/R³ | NMR: 11-Me, CO<u>CH₃</u> 8-H. etc. | mp (°C.) | yield (%) |
|---|---|---|---|---|
| 9 | −NHCH₂—(4-pyridyl) | 1.53(s), 2.45(s), 5.01(m), 4.36(d, J=6Hz, NH<u>CH₂</u>—) | 222–224 | 78 |
| 10 | −N(morpholino) | 1.56(s), 2.46(s), 5.02(m) | 223–225 | 74 |
| 11 | −N(piperazinyl)NH | 1.54(s), 2.45(s), 4.97(m) -2.3(br, piperazine) | — | 70 |
| 12 | −N(piperazinyl)N—CH₂CH₂OH | 1.55(s), 2.45(s), 4.99(m), 3.62(t, J=6Hz, CH₂CH₂OH) | 173–175 | 82 |
| 13 | −N(piperazinyl)N—(pyridyl) | 1.54(s), 2.43(s), 5.01(m), 6.55–6.75 & 8.15–8.14(pyridine) | 175–177 | 71 |

EXAMPLE 14

Lankacidin C 8-(4-methylpiperazino)carboxylate

Lankacidin C 8-iodomethylcarbonate (300 mg, prepared by the process disclosed in Japanese Published Unexamined Patent Application No. 240687/1987) was dissolved in 10 ml of tetrahydrofuran, to which 110 mg of N-methylpiperazine was added at room temperature. After stirring for 30 min. at room temperature, the reaction mixture was mixed with 50 ml of ethylacetate and washed with 60 ml of saturated aqueous sodium chloride solution. The resulting organic layer was dried over MgSO₄ and evaporated under reduced pressure to remove the solvent. The residue was subjected to silica gel column chromatography (silica gel: 60 g) eluting with chloroform-methanol (30:1). The fractions including the objective compound were collected and concentrated under reduced pressure to obtain 230 mg of the title compound.

Melting point: 201°–203° C.

Elemental analysis for $C_{31}H_{43}N_3O_8 \cdot 3/2H_2O$

Calcd.: C, 60.77; H, 7.57; N, 6.86.
Found: C, 60.82; H, 7.30; N, 6.67.

NMR (90 MHz, CDCl₃)δ: 1.25 (d, 3H, J=6 Hz), 1.38 (s, 3H), 1.54 (s, 3H), 1.92 (s, 3H), 2.1–2.7 (m, 9H), 2.46 (s, 3H), 3.4–3.7 (m, 4H), 4.2–4.6 (m, 2H), 4.70 (d, 1H, J=11 Hz), 4.8–6.0 (m, 6H), 6.17 (d, 1H, J=15 Hz), 8.07 (d, 1H, J=11 Hz).

According to the present invention, 8-lankacidin carbamate derivatives having excellent antimicrobial activities can be efficiently prepared using stable reactants of low prices.

What is claimed is:

1. A process for preparing a compound represented by the formula [III]:

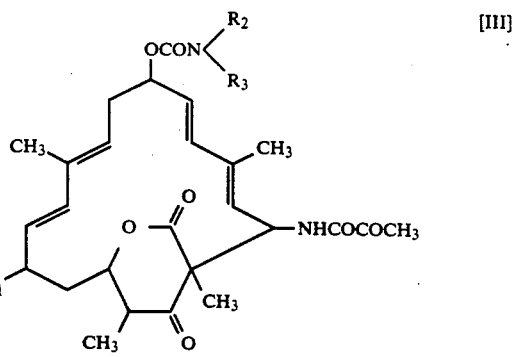

wherein $R_1$ is a hydroxy group or an alkanoyloxy group; and $R_2$ and $R_3$ are each (1) a hydrogen atom or (2) a methyl group which is unsubstituted or is substituted by pyridyl; or $R_2$ and $R_3$ together with the adjacent nitrogen atom to which they bond form a piperazino group which is unsubstituted or is substituted by methyl, hydroxymethyl, or pyridyl, or a salt thereof, comprising reaction a compound represented by the formula [I]:

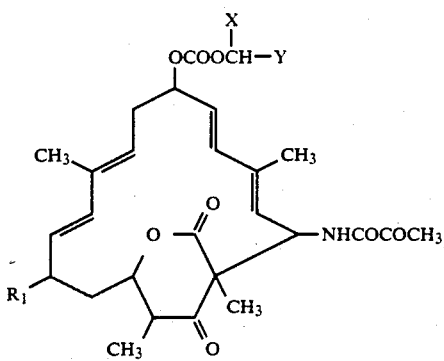

wherein $R_1$ has the same meaning as above; X is chlorine; and Y is methyl, with a compound represented by the formula [II]:

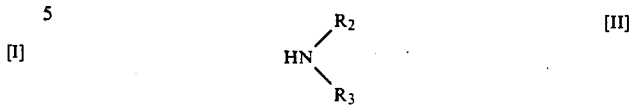

wherein $R_2$ and $R_3$ have the same meaning as above.

2. The process of claim 1 in which the reaction is conducted in an organic solvent selected from the class consisting of dichloromethane, chloroform, 1,2-dichloroethane, tetrahydrofuran, 1,4-dioxane, acetonitrile, ethyl acetate and methyl acetate.

3. The process of claim 1 wherein $R_1$ is a hydroxy or acetoxy group, and either one of $R_2$ and $R_3$ is a hydrogen atom and the remaining one is a methyl group optionally substituted by pyridyl.

* * * * *